United States Patent [19]

Oh-Kita et al.

[11] Patent Number: 4,816,603
[45] Date of Patent: Mar. 28, 1989

[54] PROCESS FOR THE PRODUCTION OF METHACROLEIN AND METHACRYLIC ACID

[75] Inventors: Motomu Oh-Kita; Yoshiyuki Taniguchi; Masaaki Kato; Masao Kobayashi, all of Otake, Japan

[73] Assignee: Mitsubishi Rayon Co., Ltd., Tokyo, Japan

[21] Appl. No.: 801,887

[22] Filed: Nov. 26, 1985

[51] Int. Cl.$^4$ .............. C07C 45/35; C07C 45/37; C07C 47/22; C07C 51/23; C07C 51/25; C07C 57/05

[52] U.S. Cl. .................. 562/538; 502/205; 502/212; 502/215; 502/220; 502/242; 502/243; 502/307; 502/308; 502/310; 562/546; 568/471; 568/477

[58] Field of Search .......... 562/538, 546; 568/471, 568/477; 502/205, 212, 215, 220, 242, 243, 307, 308, 310

[56] References Cited

U.S. PATENT DOCUMENTS

| | | | |
|---|---|---|---|
| 4,035,418 | 7/1977 | Okada et al. | 562/538 |
| 4,065,507 | 12/1977 | Hardman | 562/538 |
| 4,365,087 | 12/1982 | Kadowaki et al. | 562/546 |
| 4,380,664 | 4/1983 | Ishii et al. | 562/538 |
| 4,537,374 | 8/1985 | Sato et al. | |

FOREIGN PATENT DOCUMENTS

| | | |
|---|---|---|
| 0102641 | 3/1984 | European Pat. Off. . |
| 2420281 | 11/1984 | Fed. Rep. of Germany . |
| 2279706 | 2/1976 | France . |
| 2279465 | 2/1976 | France . |
| 2333770 | 6/1977 | France . |
| 2534904 | 4/1984 | France . |
| 2538382 | 6/1984 | France . |
| 7522660 | 2/1986 | France . |
| 1465916 | 3/1977 | United Kingdom . |
| 1518447 | 7/1978 | United Kingdom . |
| 1523141 | 8/1978 | United Kingdom . |
| 1523772 | 9/1978 | United Kingdom . |
| 2133307 | 7/1984 | United Kingdom . |

Primary Examiner—Vivian Garner
Attorney, Agent, or Firm—Armstrong, Nikaido, Marmelstein & Kubovcik

[57] ABSTRACT

The present invention provides a process for the production of methacrolein and methacrylic acid by the gas phase catalytic oxidation of isobutylene or t-butanol at high temperature using molecular oxygen in the presence of catalyst consisting of molybdenum, tungsten, bismuth, iron, nickel, antimony, and an alkali metal, to which zinc or lead is added, and further phosphorus sulfur, silicon, selenium, germanium or boron, and magnesium, cobalt, manganese or tin are added.

5 Claims, No Drawings

PROCESS FOR THE PRODUCTION OF METHACROLEIN AND METHACRYLIC ACID

BACKGROUND OF THE INVENTION

1. Field of the Invention

This invention relates to a process for the production of methacrolein and methacrylic acid by the gas phase catalytic oxidation of isobutylene or t-butanol using molecular oxygen, and more specifically to certain new catalysts used in the process thereof.

2. Description of the Prior Art

Numerous catalysts have been proposed for use in the production of methacrolein and methacrylic acid via the catalytic oxidation of isobutylene or t-butanol in a gas phase at high temperatures. For example, U.S. Pat. Nos. 4,380,664 and 4,111,984 disclose the use of MoSbBiFeNi(Sn)[K, Rb, Cs][Co, U, Ge, W, Ti] catalysts in the gas phase catalytic oxidation of isobutylene and t-butanol, respectively. Similarly, Japanese Patent Publication [Kokai] No. 27709/77 discloses the use of MoSbBiFeCo[alkali metals][Ni, Sn, Cr, Mn, Ti, W, Mg] catalysts in the gas phase catalytic oxidation of isobutylene. However, from an industrial standpoint, improvement still needs to be made in the performance of the catalysts used in this reaction, especially with regard to such properties as catalytic activity, selectivity for methacrolein and methacrylic acid, and life of the catalyst.

DETAILED DESCRIPTION OF THE INVENTION

According to the present invention, there is provided a process for the production of methacrolein and methacrylic acid comprising the gas phase catalytic oxidation of isobutylene or t-butanol using molecular oxygen in the presence of a catalyst having the formula $$Mo_a W_b Bi_c Fe_d Ni_e Sb_f X_g Y_h Z_i A_j O_k$$

wherein Mo, W, Bi, Fe, Ni, Sb, and O are respectively molybdenum, tungsten, bismuth, iron, nickel, antimony, and oxygen; X is at least one element selected from the group consisting of potassium, rubidium, and cesium; Y is at least one element selected from the group consisting of phosphorus, boron, sulfur, silicon, selenium, and germanium; Z is at least one element selected from the group consisting of zinc and lead; A is at least one element selected from the group consisting of magnesium, cobalt, manganese and tin; and a, b, c, d, e, f, g, h, i, j, and k represent the atomic ratios of the respective elements, such that when a=12, b=0.001-2 and preferably 0.01-2, c=0.01-3 and preferably 0.1-2, d=0.01-8 and preferably 0.1-5, e=0.01-10 and preferably 0.1-10, f=0.01-5 and preferably 0.1-3, g=0.01-2 and preferably 0.1-2, h=0-5 and preferably 0.001-2, i=0.01-5 and preferably 0.1-5, j=0-10 and preferably 1-10, and k is the number of oxygen atoms sufficient to satisfy the valences of the above components.

The molybdenum, tungsten, and antimony starting materials used in the preparation of catalyst employed in this invention should preferably be oxides or compounds that yield oxides under intense heating.

Examples of such compounds include ammonium molybdate, ammonium paratungstate, antimony trioxide, and the like. The starting materials for the other elements should preferably be oxides, chlorides, sulfates, nitrates, carbonates, or mixtures thereof. Known methods such as evaporation to dryness, precipitation, and oxide mixture may be employed in the preparation of the catalyst. The use of a carrier is desirable. Silica, alumina, silica/alumina, and the like may be used as the carrier.

In working the invention, molecular oxygen is added to isobutylene or t-butanol as the starting material, and gas phase catalytic oxidation carried out in the presence of the above-described catalyst. The molar ratio of isobutylene or t-butanol to oxygen should lie within the range of 1:0.5 to 1:3. The feedstock gas should be diluted with an inert gas for use. The molecular oxygen used for oxidation may be pure oxygen gas or air, although air is more advantageous for industrial applications. The reaction pressure may range from normal pressure to several atmospheres. A temperature lying within the range of 250° to 450° C. is preferable. The reaction may be conducted either on a fluid or fixed bed.

The present invention makes possible the industrially advantageous production of methacrolein and methacrylic acid from isobutylene or t-butanol, in addition to which it has the effect of providing a long catalyst life.

EXAMPLES

All references to "parts" in the examples below signify parts by weight. Analyses were carried out by gas chromatography. The conversion (%) of isobutylene or t-butanol, the selectivities (%) for methacrolein and methacrylic acid, and the combined single-pass yield (%) of (methacrolein and methacrylic acid) are defined below:

$$\text{Conversion (\%) of isobutylene or t-butanol} = \frac{\text{moles reacted}}{\text{moles fed}} \times 100$$

$$\text{Selectivity (\%) for methacrolein} = \frac{\text{moles of methacrolein produced}}{\text{moles of isobutylene or t-butanol reacted}} \times 100$$

$$\text{Selectivity (\%) for methacrylic acid} = \frac{\text{moles of methacrylic acid produced}}{\text{moles of isobutylene or t-butanol reacted}} \times 100$$

$$\text{Single-pass yield (\%) of methacrolein + methacrylic acid} = \frac{\text{moles of (methacrolein + methacrylic acid) produced}}{\text{moles of isobutylene or t-butanol fed}} \times 100$$

EXAMPLE 1

Ammonium molybdate (500 parts), 18.5 g of ammonium paratungstate, and 27.8 g of rubidium nitrate were added to 1000 parts of water, and the mixture heated under stirring, giving solution A.

In a separate step, 250 parts of 60% nitric acid was added to 850 parts of water, then 114.5 parts of bismuth nitrate added and dissolved in this. This was followed by the successive addition and dissolution of 286.0 parts ferric nitrate, 480.4 parts nickel nitrate, 90.8 parts magnesium nitrate, and 35.1 parts zinc nitrate, giving solution B.

After adding solution B to solution A, 51.6 parts of antimony trioxide was added to the resulting slurry, the mixture heated under stirring, and most of the water evaporated off. The cake-like substance obtained was dried at 120° C. and molded by calcining for ten hours at 500° C. The composition of the catalyst thus obtained was $Mo_{12}W_{0.3}Bi_1Fe_3Ni_7Mg_{1.5}Zn_{0.5}Sb_{1.5}Rb_{0.8}O_x$. Since the atomic ratio X for oxygen is determined naturally by the valences of the other elements, this is omitted hereafter.

This catalyst was packed into a stainless steel reactor and a gas mixture consisting of isobutylene (5%), oxygen (12%), steam (10%), and nitrogen (73%) was passed through the catalyst layer for a contact period of 2 seconds and reacted at 365° C.

The conversion of isobutylene was 95%, the selectivity for methacrolein 87%, the selectivity for methacrylic acid 4.8%, and the single pass yield for methacrolein and methacrylic acid combined was 87.2%.

EXAMPLE 2

Using the catalyst in Example 1 and t-butanol as the starting material, a reaction was carried out under the same conditions as in Example 1. This reaction gave a t-butanol conversion of 100%, a selectivity for methacrolein of 85.5%, a selectivity for methacrylic acid of 2.8%, and a combined single-pass yield for methacrolein and methacrylic acid of 88.3%.

EXAMPLES 3-11

The following catalysts were prepared in the same manner as in Example 1.
Example 3: $Mo_{12}W_{0.3}Bi_{0.8}Fe_{2.5}Ni_3Co_4Sn_1Pb_{0.5}Sb_{1.3}K_{0.1}Cs_{0.7}$
Example 4: $Mo_{12}W_{0.5}Bi_{0.8}Fe_3Ni_5Co_1Mg_1Zn_1B_{0.5}Sb_{1.5}Cs_{0.7}$
Example 5: $Mo_{12}W_{0.5}Bi_1Fe_{2.7}Ni_7Mn_{0.5}Co_1P_{0.05}Sb_2Rb_{0.5}Zn_1$
Example 6: $Mo_{12}W_{0.5}Bi_1Fe_3Ni_7Mn_1Mg_2Zn_{0.5}S_{0.2}Sb_1Rb_{0.2}Cs_{0.3}$
Example 7: $Mo_{12}W_{0.2}Bi_{0.7}Fe_3Ni_7Mg_1Pb_1Si_{0.8}Sb_{1.5}K_{0.3}$
Example 8: $Mo_{12}W_{0.5}Bi_{0.9}Fe_{2.7}Ni_1Co_5Pb_1Si_{0.8}Se_{0.8}Sb_{1.5}Cs_{0.7}$
Example 9: $Mo_{12}W_{0.1}Bi_1Fe_3Ni_8Zn_1Sn_1Ge_{0.1}Sb_1Rb_{0.5}K_{0.5}$
Example 10: $Mo_{12}W_{0.5}Bi_1Fe_3Ni_{6.5}Rb_{0.7}Sb_2Pb_2$
Example 11: $Mo_{12}W_{0.5}Bi_1Fe_{2.5}Ni_7P_{0.08}Zn_2Pb_{0.5}Sb_{1.2}Cs_{0.7}$ Using these catalysts, reactions were carried out under the same reaction conditions as in Example 1, save for the reaction temperature. The results are given in Table 1.

TABLE 1

|  | Reaction Temp. (°C.) | Conversion of isobutylene (%) | Selectivity for methacrolein (%) | Selectivity for methacrylic acid (%) | Single-pass yield of (methacrolein + methacrylic acid) (%) |
|---|---|---|---|---|---|
| Example 3 | 365 | 95.5 | 86 | 5.2 | 87.1 |
| Example 4 | 365 | 96 | 88 | 3.5 | 87.8 |
| Example 5 | 370 | 93 | 89 | 4.3 | 86.8 |
| Example 6 | 370 | 93 | 91 | 2.5 | 87.0 |
| Example 7 | 370 | 95 | 86 | 4.9 | 86.4 |
| Example 8 | 365 | 96 | 87 | 4 | 87.4 |
| Example 9 | 360 | 92 | 90 | 4.5 | 86.9 |
| Example 10 | 370 | 94.5 | 86 | 5 | 86.0 |
| Example 11 | 370 | 95 | 87 | 3.8 | 86.3 |

EXAMPLES 12-20

These reactions were carried out on t-butanol as the starting material using the respective catalysts in Examples 3-11. All the other reaction conditions were the same as in the corresponding examples above. The results are given below in Table 2.

TABLE 2

|  | Reaction Temp. (°C.) | Conversion of t-butanol (%) | Selectivity for methacrolein (%) | Selectivity for methacrylic acid (%) | Single-pass yield of (methacrolein + methacrylic acid) (%) |
|---|---|---|---|---|---|
| Example 12 | 365 | 100 | 85 | 3.0 | 88.0 |
| Example 13 | 365 | 100 | 86 | 2.8 | 88.8 |
| Example 14 | 370 | 100 | 85.5 | 3.0 | 88.5 |
| Example 15 | 370 | 100 | 86 | 1.5 | 87.5 |
| Example 16 | 370 | 100 | 85 | 2.9 | 87.9 |
| Example 17 | 365 | 100 | 85 | 2.5 | 87.5 |
| Example 18 | 360 | 100 | 86 | 1.5 | 87.5 |
| Example 19 | 370 | 100 | 84 | 3.0 | 87.0 |
| Example 20 | 370 | 100 | 85 | 2.5 | 87.5 |

COMPARATIVE EXAMPLE 1

A catalyst having the composition $Mo_{12}Bi_1Fe_3Ni_7Mg_{1.5}Zn_{0.5}Sb_{1.5}Rb_{0.8}$ was prepared in the same manner as in Example 1, but without using the 18.5 parts of ammonium paratungstate. A reaction was conducted using this catalyst under the same reaction conditions as in Example 1, giving an isobutylene conversion of 91%, a selectivity for methacrolein of 86%, a selectivity for methacrylic acid of 5.3%, and a single-pass yield for methacrolein and methacrylic acid combined of 83.1%.

The process was repeated in the same fashion using t-butanol, giving a t-butanol conversion of 100%, a selectivity for methacrolein of 80%, a selectivity for methacrylic acid of 3.6%, and a single-pass yield for methacrolein and methacrylic acid combined of 83.6%.

COMPARATIVE EXAMPLE 2

A catalyst having the composition $Mo_{12}W_3Bi_1Fe_3Ni_7Sb_{1.5}Rb_{0.8}Mg_{1.5}Zn_{0.5}$ was prepared in the same manner as in Example 1, except for the amount of ammonium paratungstate, which was increased to 184.8 parts. A reaction was conducted using this catalyst under the same reaction conditions as in Example 1, giving an isobutylene conversion of 70%, a selectivity for methacrolein of 75%, a selectivity for methacrylic acid of 5%, and a single-pass yield for methacrolein and methacrylic acid combined of 56.0%. In addition, the same reaction as in Example 2 was carried out, giving a t-butanol conversion of 100%, a selectivity for methacrolein of 58%, a selectivity for methacrylic acid of 2.8%, and a single-pass yield for methacrolein and methacrylic acid combined of 60.8%.

COMPARATIVE EXAMPLE 3

A catalyst having the composition $Mo_{12}W_{0.3}Bi_1Fe_3Ni_7Sb_{1.5}Rb_{0.8}$ was prepared in the same manner as in Example 1, but without using the 90.8 parts of magnesium nitrate and 35.1 parts of zinc nitrate. A reaction was conducted using this catalyst under the same reaction conditions as in Example 1, giving an isobutylene conversion of 90%, a selectivity for methacrolein of 84%, a selectivity for methacrylic acid of 5%, and a single-pass yield for methacrolein and methacrylic acid combined of 80.1%. In addition, the same reaction as in Example 2 was carried out, giving a t-butanol conversion of 100%, a selectivity for methacrolein of 76%, a selectivity for methacrylic acid of 5.2%, and a single-pass yield for methacrolein and methacrylic acid combined of 81.2%.

COMPARATIVE EXAMPLE 4

A catalyst having the composition $Mo_{12}W_{0.3}Bi_4Fe_3Ni_7Mg_{1.5}Zn_{0.5}Sb_{1.5}Rb_{0.8}$ was prepared in the same manner as in Example 1, except for the amount of bismuth nitrate, which was increased to 457.9 parts. A reaction was conducted using this catalyst under the same reaction conditions as in Example 1, giving an isobutylene conversion of 75%, a selectivity for methacrolein of 78%, a selectivity for methacrylic acid of 3%, and a single-pass yield for methacrolein and methacrylic acid combined of 60.8%. In addition, the same reaction as in Example 2 was carried out, giving a t-butanol conversion of 100%, a selectivity for methacrolein of 60%, a selectivity for methacrylic acid of 1.6%, and a single-pass yield for methacrolein and methacrylic acid combined of 61.6%.

COMPARATIVE EXAMPLE 5

A catalyst having the composition $Mo_{12}W_{0.3}Bi_1Fe_3Ni_7Mg_{1.5}Zn_{0.5}Sb_{1.5}Rb_{2.5}$ was prepared in the same manner as in Example 1, except for the amount of rubidium nitrate, which was increased to 87.0 parts. A reaction was conducted using this catalyst under the same reaction conditions as in Example 1, giving an isobutylene conversion of 70%, a selectivity for methacrolein of 80%, a selectivity for methacrylic acid of 4%, and a single-pass yield for methacrolein and methacrylic acid combined of 58.8%. In addition, the same reaction as in Example 2 was carried out, giving a t-butanol conversion of 100%, a selectivity for methacrolein of 58.5%, a selectivity for methacrylic acid of 2.3%, and a single-pass yield for methacrolein and methacrylic acid combined of 60.8%.

EXAMPLE 21

Reactions were conducted for 9000 hours under the same reaction conditions as in Example 1 using the catalysts in Examples 1 and 4. The results are given in Table 3.

TABLE 3

| | Reaction time (elapsed) | Conversion of isobutylene (%) | Selectivity for methacrolein (%) | Selectivity for methacrylic acid (%) | Single-pass yield of (methacrolein + methacrylic acid) (%) |
|---|---|---|---|---|---|
| Example 1 catalyst | 5 hrs | 95 | 87 | 4.8 | 87.2 |
| | 9000 hrs | 94.5 | 86.8 | 4.8 | 86.6 |
| Example 4 catalyst | 5 hrs | 96 | 88 | 3.5 | 87.8 |
| | 9000 hrs | 95 | 88 | 4.0 | 87.4 |

EXAMPLE 22

Reactions were conducted for 9000 hours under the same reaction conditions as in Example 2 using the catalysts in Examples 1 and 4. The results are given in Table 4.

TABLE 4

| | Reaction time (elapsed) | Conversion of t-butanol (%) | Selectivity for methacrolein (%) | Selectivity for methacrylic acid (%) | Single-pass yield of (methacrolein + methacrylic acid) (%) |
|---|---|---|---|---|---|
| Example 1 catalyst | 5 hrs | 100 | 85.5 | 2.8 | 88.3 |
| | 9000 hrs | 100 | 85 | 2.5 | 87.5 |
| Example 4 catalyst | 5 hrs | 100 | 86 | 2.8 | 88.8 |
| | 9000 hrs | 100 | 85.5 | 2.5 | 88.0 |

COMPARATIVE EXAMPLE 6

Table 5 gives the results obtained by running reactions for 9000 hours under the same reaction conditions as in Example 1 using the catalysts in Comparative Examples 1-5.

TABLE 5

| | Reaction time (elapsed) | Conversion of isobutylene (%) | Selectivity for methacrolein (%) | Selectivity for methacrylic acid (%) | Single-pass yield of (methacrolein + methacrylic acid) (%) |
|---|---|---|---|---|---|
| Comparative Example 1 catalyst | 5 hrs | 91 | 86 | 5.3 | 83.1 |
| | 9000 hrs | 90 | 84 | 5 | 80.1 |
| Comparative Example 2 catalyst | 5 hrs | 70 | 75 | 5 | 56.0 |
| | 9000 hrs | 60 | 75 | 5 | 48.0 |
| Comparative Example 3 catalyst | 5 hrs | 90 | 84 | 5 | 80.1 |
| | 9000 hrs | 88 | 82 | 5 | 76.6 |
| Comparative Example 4 catalyst | 5 hrs | 75 | 78 | 3 | 60.8 |
| | 9000 hrs | 70 | 77 | 4 | 56.7 |
| Comparative Example 5 catalyst | 5 hrs | 70 | 80 | 4 | 58.8 |
| | 9000 hrs | 68 | 79 | 5 | 57.1 |

Table 6 gives the results obtained by conducting reactions for 9000 hours under the same reaction conditions as in Example 2 using the catalysts in Comparative Examples 1-5.

TABLE 6

| | Reaction time (elapsed) | Conversion of t-butanol (%) | Selectivity for methacrolein (%) | Selectivity for methacrylic acid (%) | Single-pass yield of (methacrolein + methacrylic acid) (%) |
|---|---|---|---|---|---|
| Comparative Example 1 catalyst | 5 hrs | 100 | 80 | 3.6 | 83.6 |
| | 9000 hrs | 100 | 78.4 | 4.6 | 83.0 |
| Comparative Example 2 catalyst | 5 hrs | 100 | 58.4 | 2.4 | 60.8 |
| | 9000 hrs | 100 | 54 | 2.3 | 56.3 |
| Comparative Example 3 catalyst | 5 hrs | 100 | 76 | 5.2 | 81.2 |
| | 9000 hrs | 100 | 72.8 | 5.1 | 77.9 |
| Comparative Example 4 catalyst | 5 hrs | 100 | 60 | 1.6 | 61.6 |
| | 9000 hrs | 100 | 56.2 | 1.5 | 57.7 |
| Comparative Example 5 catalyst | 5 hrs | 100 | 58.5 | 2.3 | 60.8 |
| | 9000 hrs | 100 | 53.3 | 1.4 | 54.7 |

We claim:

1. A process for the production of methacrolein and methacrylic acid comprising the gas phase catalytic oxidation of isobutylene or t-butanol using molecular oxygen in the presence of a catalyst having the composition $$Mo_aW_bBi_cFe_dNi_eSb_fX_gY_hZ_iA_jO_k$$

wherein Mo, W, Bi, Fe, Ni, Sb, and O are respectively molybdenum, tungsten, bismuth, iron, nickel, antimony, and oxygen; X is at least one element selected from the group consisting of potassium, rubidium, and cesium; Y is at least one element selected from the group consisting of phosphorus, boron, sulfur, silicon, selenium, and germanium; Z is at least one element selected from the group consisting of zinc and lead; A is at least one element selected from the group consisting of magnesium, cobalt, manganese, and tin; and a, b, c, d, e, f, g, h, i, j, and k represent the atomic ratios of the respective elements, and a=12, b=0.001-2, c=0.01-3, d=0.01-8, e=0.01-10, f=0.01-5, g=0.01-2, h=0-5, i=0.01-5, j=0-10, and k is the number of oxygen atoms sufficient to satisfy the valences of the above components.

2. A process according to claim 1 wherein the catalyst employed contains zinc as the Z component.

3. A process according to claim 1 wherein the catalyst employed contains zinc as the Z component and cobalt as the A component.

4. A process according to claim 1 wherein the catalyst employed contains phosphorus or boron as the Y component.

5. A process according to claim 1, wherein b=0.01-2, c=0.1-2, d=0.1-5, e=0.1-10, f=0.1-3, g=0.1-2, h=0.001-2, i=0.1-5, and j=1-10.

* * * * *